US008735083B2

(12) United States Patent
Watzele et al.

(10) Patent No.: US 8,735,083 B2
(45) Date of Patent: May 27, 2014

(54) INHIBITION OF PEROXIDASE ENZYMATIC ACTIVITY

(75) Inventors: Manfred Watzele, Weilheim (DE);
Bernd Buchberger, Peissenberg (DE);
Claudia Kirr, Wielenbach (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 60 days.

(21) Appl. No.: 11/758,854

(22) Filed: Jun. 6, 2007

(65) Prior Publication Data

US 2007/0292905 A1    Dec. 20, 2007

(30) Foreign Application Priority Data

Jun. 9, 2006 (EP) ..................... 06011949

(51) Int. Cl.
*G01N 33/53*   (2006.01)
*C12N 9/99*   (2006.01)

(52) U.S. Cl.
USPC ........................... 435/7.92; 435/25; 435/184

(58) Field of Classification Search
None
See application file for complete search history.

(56) References Cited

U.S. PATENT DOCUMENTS

| 4,234,680 | A | 11/1980 | Hevey et al. |
| 4,448,882 | A | 5/1984 | Brodbeck et al. |
| 4,752,570 | A | 6/1988 | Wehner et al. |
| 5,294,535 | A | 3/1994 | Gribnau et al. |
| 5,405,750 | A * | 4/1995 | Suciu-Foca et al. ......... 435/7.24 |
| 2004/0219620 | A1 | 11/2004 | Mayer |
| 2005/0175608 | A1 * | 8/2005 | Tamura et al. ............. 424/145.1 |

OTHER PUBLICATIONS

Instructions for One Step ABTS, Pierce Chemical Co., 2005.*
The Comparison of ABTS, TMB and OPD Peroxidase Substrate Systems, Technical Service Report, KPL Labs, 2002.*
ABTS Peroxidase Stop Solution, KPL Labs Catalog, 2004.*
Cacace, M.G. et al., "The Hofmeister Series: Salt and Solvent Effects on Interfacial Phenomena," Quarterly Reviews of Biophysics 30, 3 (1997), 241-277.
Schomburg, D. et al., Enzyme Handbook 7, Springer-Verlag Berlin Heidelberg, 1994, EC 1.11.7:1-6.
Shannon, L. et al., "Peroxidase Isozymes from Horseradish Roots," The Journal of Biological Chemistry, vol. 241, No. 9, May 10, 1966, 2166-2172.
Welinder, K. et al., "Amino Acid Sequence Studies of Horseradish Peroxidase; Amino and Carboxyl Termini, Cyanogen Bromide and Tryptic Fragments, the Complete Sequence, and Some Structural Characteristics of Horseradish Peroxidase C," Eur. J. Biochem, 96, 483-502 (1979).
Zollner, H., Handbook of Enzyme Inhibitors, 2nd Ed. Graz, (1989) Part A: 367-368.
Moosavi-Movahedi, A. A. et al., "Thermodynamics of denaturation of horseradish peroxidase with sodium ndodecyl sulphate and n-dodecyl trimethlammonium bromide," Colloids and Surfaces B: Biointerfaces, 1997, vol. 9, pp. 123-130.

* cited by examiner

*Primary Examiner* — Lisa J Hobbs
(74) *Attorney, Agent, or Firm* — Dinsmore & Shohl LLP

(57) ABSTRACT

The present invention deals with reagents and compositions capable of effectively inhibiting peroxidase activity. According to the invention, peroxidase enzymatic activity is blocked with an acidic aqueous solution of a protein denaturing agent. preferred protein denaturing agents are detergents and chaotropic substances.

5 Claims, 2 Drawing Sheets

INHIBITION OF PEROXIDASE ENZYMATIC ACTIVITY

RELATED APPLICATIONS

This application claims priority to European application EP 06011949.2 filed Jun. 9, 2006.

FIELD OF THE INVENTION

The present invention deals with reagents and compositions capable of effectively inhibiting peroxidase activity. In particular, the invention relates to blocking peroxidase enzymatic activity with an acidic aqueous solution comprising a protein denaturing agent, in particular, a detergent or chaotropic substance.

BACKGROUND

A peroxidase is an enzyme, which may contain heme, that catalyzes a reaction of the form:

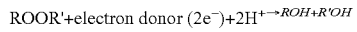

ROOR'+electron donor $(2e^-)+2H^+ \rightarrow ROH+R'OH$

For many of these enzymes the optimal ROOR' (electron acceptor) substrate is hydrogen peroxide, but others are more active with organic hydroperoxides such as lipid peroxides.

The nature of the electron donor is very dependent on the structure of the enzyme. For example, horseradish peroxidase (HRP), which is isolated from horseradish (*Armoracia rusticana*) roots, can use a variety of organic compounds as electron donors and acceptors.

Being a member of the ferroprotoporphyrin group of peroxidases, hRP does contain a heme group. Located at positions distal and proximal to the heme plane there are in addition two calcium binding sites. HRP C dominates quantitatively among the isoperoxidases of horseradish root. HRP C is a single chain polypeptide comprising 308 amino acid residues which form four internal disulfide bridges and 8 neutral carbohydrate side-chains. The molecular weight of the polypeptide chain is 33890 Daltons (Da), and the molecular weight of native horseradish peroxidase C is about 44 kDa (Welinder, K. G., Eur. J. Biochem. 96 (1979) 483-502). At least seven isozymes of HRP exist (Shannon, L. M., et al., J. Biol. Chem. 241 (1966) 2166-2172). The carbohydrate composition consists of galactose, arabinose, xylose, fucose, mannose, mannosamine, and galaciosamine, depending upon the specific isozyme (Shannon, L. M., et al., J. Biol. Chem. 241 (1966) 2166-2172). The isoelectric point of the isozymes ranges from 3.0 to 9.0.

The pH optimum of HRP is in the range of pH 6.0 to pH 6.5; activity at pH 7.5 is 84% of the maximum. The enzyme is most stable in the range of pH 5.0 to pH 9.0 (Schomburg, D., et al., Enzyme Handbook 7 (1994) EC 1.11.1.7:1-6).

HRP combines with hydrogen peroxide ($H_2O_2$) and the resultant [HRP-$H_2O_2$] complex can oxidize a wide variety of chromogenic hydrogen donors. HRP has a broad and accessible active site and many chemically very different compounds can reach the site of the reaction. Known HRP substrates include TMB (3,3',5,5'-tetramethylbenzidine), ABTS (2,2'-azino-di-(3-ethylbenzthiazoline-6-sulphonic acid diammonium salt), luminol (5-amino-1,2,3,4-tetrahydrophthalazin-1,4-dion) and isoluminol (4-aminophthalhydrazide), as well as fluorogenic substrates such as tyramine (4-hydroxy-phenethylamine), homovanillic acid, and 4-hydroxyphenyl acetic acid. Further HRP substrates are known to the art. Due to its versatility, HRP is commercially used as a component of immunoassays, such as coupled enzyme assays, chemiluminescent assays and assay kits for clinical diagnostics including histochemistry kits.

In a typical example, an immunoassay based on a sandwich ELISA principle and using analyte-specific coating and capture antibodies includes hRP conjugated to the capture antibody. The peroxidase enzyme catalyzes the cleavage of a chromogenic substrate to yield a product which can be measured spectrophotometrically. The absorbance of the a colored or fluorescent product is directly correlated to the amount of analyte in the sample analyzed. In order to allow the comparison of simultaneous measurements including controls, the HRP enzymatic reaction needs to be terminated after a defined incubation period. To this end a stop reagent is used. Stop reagents have to fulfil two major requirements: (1) to terminate the reaction by effectively inhibiting the enzymatic activity of HRP; (2) to stabilize the oxidized products of the chromogenic or fluorogenic substrate(s).

In Zollner, H., Handbook of enzyme Inhibitors, 2nd Ed. (1989) part A: 367-368) the following compounds have been described as inhibitors of HRP; sodium azide, cyanide, L-cystine, dichromate, ethylenethiourea, hydroxylamine, sulfide, vanadate, p-aminobenzoic acid, $Cd^{+2}$, $Co^{+2}$, $Cu^{+2}$, $Fe^{+3}$, $Mn^{+2}$, $Ni^{+2}$, $Pb^{+2}$. Many stop reagents known to the art make use of these compounds. Another known reagent used to stop the HRP activity is oxalic acid.

When designing a stop reagent for reactions catalyzed by HRP, bleaching of the color brought about by the chromogenic substance is a frequent problem. The use of heavy metal salts in stop reagents has a number of disadvantages including toxicity. Also, certain salts of heavy metals are explosive as dry materials. Another known stop reagent for the HRP reaction is formaldehyde. However, the stabilizing effect of this compound is unsatisfactory. In addition, formaldehyde is toxic and has a troublesome smell.

U.S. Pat. No. 4,234,680 teaches the use of an alkali metal bisulphite as stop reagent. However, this reducing agent has the potential of decolorizing the oxidized products formed from certain chromogenic substrates by the HRP catalyzed reaction. This applies especially to the oxidized products of ABTS and related salts.

In U.S. Pat. No. 4,752,570 a process for the determination of peroxidase is described, wherein a chromogenic substrate reaction is stopped by adding catalase as stop reagent. This process, however, requires the use of an enzyme with limited stability and causes foaming due to the release of oxygen. Foaming may interfere with spectrophotometric readings.

Finally, surface-active agents, such as secondary alkyl sulphate or dodecyl hydrogen sulphate, have been suggested as stop agents. For example, SDS (sodium dodecyl sulphate) at a final concentration in solution of 0.5% [w/v] is suggested for stopping the color formation using HRP and ABTS, see pack insert of products #11684302 (catalogue of Roche Diagnostics GmbH, Mannheim, Germany). Similarly, an SDS solution is supplied from KPL laboratories for the same purpose. However, these compounds are not able to fully suppress further color formation and/or lead to precipitation of the substrate. Results presented in Example 1 illustrates this fact.

Also strong (mineral) acids are used as stop reagents to inhibit peroxidase enzymatic activity. This is especially the case when 3,3'-5,5' tetramethylbenzidine serves as a color substrate and the peroxidase enzyme is inhibited ba adjusting the pH to values of pH 2 or even lower.

Several reagents that are described above lead to precipitation of colored substrates like ABTS and cause erroneous readings, e.g. spectrophotometric readings of ELISA plates. Precipitation particularly occurs when using strong acids at pH values lower than 2. In addition, 1 M $H_2SO_4$ changes the color of the substrate 3,3'-5,5'-tetramethylbenzidine from blue to yellow. Other inhibitors (e.g. bisulphate, see above) may lead to bleaching and therefore are of limited use. Furthermore, certain stop reagent sonly after a certain lag phase achieve inhibition or just lead to an incomplete inhibition of the HRP-catalyzed reaction.

It is an object of the present invention to overcome the disadvantages of the stop reagents of the state of the art. It is a particular object of the present invention to provide an improved stop reagent for HRP-catalyzed reactions. Another object of the invention is to provide a process for the determination of peroxidase enzymatic activity in a sample.

SUMMARY OF THE INVENTION

A first embodiment of the invention is the use of an acidic aqueous solution of a protein denaturing agent to inhibit peroxidase enzymatic activity. A further embodiment of the invention is a composition comprising (a) a peroxidase enzyme, (b) an electron acceptor substrate, (c) an electron donor substrate, and (d) a protein denaturing agent, characterized in that the composition is an acidic aqueous solution. Yet, a further embodiment of the invention is a method to inhibit peroxidase enzymatic activity in an aqueous solution comprising a peroxidase enzyme, an electron acceptor substrate, and an electron donor substrate, characterized in that the composition is mixed with an acidic aqueous solution of a denaturing agent, whereby in the resulting mixture the pH is adjusted to a final value of pH 2.5 to pH 4.2. Yet, a further embodiment of the invention is a kit comprising (a) a conjugate comprising horseradish peroxidase, (b) an acidic solution containing a protein denaturing agent. Yet, a further embodiment of the invention is a method to determine the amount of peroxidase enzymatic activity in a sample, comprising the steps of (a) adding to the sample an electron acceptor substrate and an electron donor substrate, whereby the electron donor substrate forms a dye or a pigment upon oxidation; (b) incubating the sample, whereby the peroxidase enzymatic activity catalyzes the oxidation of the electron donor substrate; (c) inhibiting the peroxidase enzymatic activity by way of mixing with the sample an acidic aqueous solution of a protein denaturing agent, whereby the pH value of the mixture is adjusted at an acidic ph; (d) determining the amount of dye or pigment formed; (e) correlating the amount of dye of pigment with the amount of peroxidase enzymatic activity in the sample.

DETAILED DESCRIPTION OF THE INVENTION

Figure 1A:
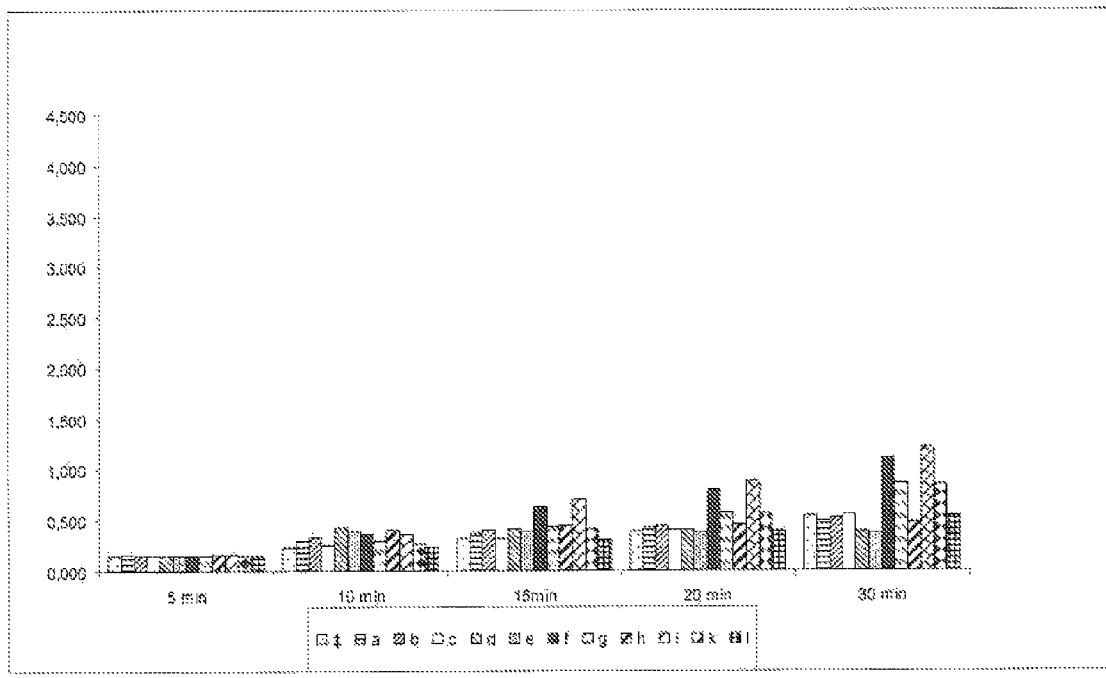
FIG. 1, A and B: inhibition of ABTS turnover catalyzed by a low amount of HRP (detection of a low amount of mono-and oligosomes in Jurkat cells; further details are given in Example 1). The ordinate indicates absorbance. Groups of bars represent comparative measurements at time points after the addition of stop reagents as indicated: (‡)—control, ABTS solution incubated without HRP, no stop reagent added; (a) to (k)—ABTS solution incubated with HRP and subsequently mixed with stop reagent as indicated: (a) 1% SDS, (b) 5% SDS, (c) distilled water, (d) 0.5 M $H_2SO_4$, (e) 0.25 M $H_2SO_4$, (f) 0.1 M $H_2SO_4$, (g) 0.05 M $H_2SO_4$, (h) 0.25 M oxalic acid, (i) 0.1 M oxalic acid, (k) 0.05 M oxalic acid, (l) distilled water.

Certain terms are used with particular meaning, or are defined for the first time, in this description of the present invention. For the purposes of the present invention, the terms are defined by their art-accepted definitions, when such exist, that when those definitions conflict or partially conflict with the definitions set forth below. In the event of a conflict in definition, the meaning of the terms are first defined by the definitions set forth below.

The term "comprising" is used in the description of the invention and in the claims to mean "including, but not necessarily limited to".

Horseradish peroxidase is also referred to as "HRP". Generally, the mixture of horseradish peroxidase isoenzymes isolated from horseradish roots is within the meaning of the term HRP. However, the term HRP also encompasses enriched, isolated, or recombinantly produced HRP C isoenzyme. Peroxidase (particularly HRP) activity can be assayed in a "reaction mixture" which comprises in an aqueous solution (a) a peroxidase enzyme, (b) an electron acceptor substrate, and (c) an electron donor substrate, whereby the salt content and the pH of the aqueous solution permit the peroxidase enzyme to catalyze the transfer of electrons from the electron donor substrate to the electron acceptor substrate. Regarding the electron donor substrate the invention generally contemplates compounds which upon oxidation form a dye or a pigment. Thus, the invention encompasses stop reagents for peroxidase-catalyzed reactions using (1) chromogenic, (2) fluorogenic, and (3) light emitting electron donor substrates. Such substrates are well known to the art.

As used herein, the term "stop reagent" refers to a reagent for terminating or inhibiting in a reaction mixture the chemical reaction catalyzed by HRP. In addition, the stop reagent stabilized the chemical entities formed by the chemical reaction catalyzed by HRP, so that the amount of oxidized reaction product(s) of the reaction can be determined following the addition of the stop reagent to the reaction mixture. It is understood that the stop reagent according to the invention itself usually comprises a mixture of different compounds.

According to the present invention, a "protein denaturing agent" or "denaturing agent" is a chemical compound capable of denaturing proteins in aqueous solution. Denaturation is usually effected by changing the secondary or tertiary structure of the protein, particularly HRP. Thus, certain detergents are capable of changing the structure of HRP. The same result can be obtained by changing the interaction of the protein (HRP) with the solvent (water), e.g. by way of adding chaotropic substances. A high concentration of a chaotropic substance changes the bulk properties of water (Cacace, M. G., et al., Quarterly Review of Biophysics 30 (1997) 241-277) by weakening hydrophobic interactions, thereby causing proteins to denature. Whether effected by a detergent or a chaotropic substance, denaturation is not necessarily quantitative. Denaturation may be dependent, e.g. on the concentration of the protein denaturing agent.

A first embodiment of the invention is the use of an acidic aqueous solution of a protein denaturing agent as a stop reagent to inhibit peroxidase enzymatic activity. As the skilled person appreciates, the stop reagent of the present invention is capable of stopping of the color formation in a peroxidase reaction mixture at a definite, predetermined point of time. The stop reagent of the invention is immediately effective and does not result in a disadvantageous change of the color present at the point of time of its addition to the reaction mixture.

The stop reagent of the invention comprises at least two essential components, wherein the first essential components shifts the ph of the reaction mixture to a value between 2.5 and 4.2, but without leading to the precipitation of the reaction products. That is to say, the reaction mixture is acidified mildly thereby avoiding precipitation of any member of the reaction mixture. According to the invention an aqueous solution comprising a protein denaturing agent is used to inhibit peroxidase enzymatic activity, whereby, the pH of the aqueous solution is preferably between pH 2.5 and pH 4.2. More preferred, the pH is between 2.7 and 3.8, even more preferred, between pH 3 and pH 3.5. Another preferred ph range of the aqueous solution is between pH 2.5 and pH 3. Yet, another preferred ph range of the aqueous solution is between pH 3 and pH 4.2.

The second essential component of the stop reagent is a protein denaturing agent which preferably is a detergent or a chaotropic substance. A preferred detergent is selected from the group consisting of SDS (sodium dodecylsulfate), N-Laurylsarcosin, cetyltrimethylammonnium bromide (CTAB), and dodecyltrimethylamonnium bromide (DTAB) as well as mixtures thereof. A preferred chaotropic substance is selected from the group consisting of urea or guanidinium hydrochloride, guanidinium isothiocyanate, and guanidinium thiocyanate, as well as mixtures thereof. Taken alone each of the said protein genaturing agents will not lead to a immediate and complete inhibition at the concentration applied. The surprising finding by the inventors was, however, that the combination of any one of the protein denaturants combined with an acidic pAh leads to an exceptionally effective inhibition of peroxidase enzymatic activity.

Another embodiment of the invention is a method to inhibit peroxidase enzymatic activity in an aqueous solution comprising a peroxidase enzyme, an electron acceptor substrate, and an electron donor substrate, characterized in that the composition is mixed with an acidic aqueous solution of a denaturing agent, whereby in the resulting mixture the pH is adjusted to a final value of pH 2.5 to pH 4.2. It is preferred that the final concentration of the denaturing agent is 0.25 to 10% weight by volume when the denaturing agent is a detergent. In case the denaturing agent is a chaotropic substance the preferred concentration is 5% to 70% weight by volume. In order to achieve very good HRP inactivation, it is very much preferred to inhibit peroxidase enzymatic activity in the reaction mixture with SDS at a final concentration between 0.25% and 10% weight by volume, most preferred between 0.5% and 2.5% weight by volume. Thus, applying the method of the invention requires the skilled person to form a composition of the invention, the composition comprising (a) a peroxidase enzyme, (b) an electron acceptor substrate, (c) an electron donor substrate, and (d) a protein denaturing agent, characterized in that the composition is an acidic aqueous solution.

In a preferred embodiment, the electron donor substrate is a chromogenic, chemiluminescent or fluorogenic compound. The stop solution of the present invention can be used with the electron donor substrates known to the art for carrying out HRP determinations. Typical examples of frequently used electron donor substrates include 2,2'-azino-di-(3-ethylbenzthiazoline-6-sulphonic acid) diammonium salt (ABTS), 3,3'-5,5'-tetramethylbenzidine (IMB), 4-hydroxy-phenethylamine (tyramine), 4-hydroxyphenyl acetic acid, homovanillic acid, o-pheylenediamine, p-phenylenediamine, m-aminosalicylic acid, dianisidine, p-aminobenzoic acid, aniline, 4-aminoantipyrine and the like. These chromogens are well known for HRP determinations and do not here require any further explanation.

Usually the electron acceptor substrate is hydrogen peroxide. However, other electron acceptor substrates are possible.

The present invention also provides a process for the determination of peroxidase. An example therefor is an enzyme immunoassay in which an immobilized analyte is qualitatively or quantitatively detected by means of an antibody or antibody fragment conjugated to one or more peroxidase enzymes. In such a case the amount of bound peroxidase is proportional to the amount of analyte. Such an assay requires reacting the peroxidase with a peroxide and a substrate, and kinetic or end point measurement of the color resulting from the oxidation of the chromogen. In such assays color formation needs to be stopped after a definite period of time by the addition of a stop agent. Thus, a further embodiment of the invention is a method to determine the amount of peroxidase enzymatic activity in a sample, comprising the steps of (a) adding to the sample an electron acceptor substrate and an electron donor substrate, whereby the electron donor substrate forms a dye or a pigment upon oxidation; (b) incubating the sample, whereby the peroxidase enzymatic activity catalayzes the oxidation of the electron donor substrate; (c) inhibiting the peroxidase enzymatic activity by way of adding to the sample an acidic aqueous solution of a protein denaturing agent; (d) determining the amount of dye of pigment formed; (e) correlating the amount of dye or pigment with the amount of peroxidase enzymatic activity in the sample.

A further embodiment of the invention is a kit comprising (a) a conjugate comprising horseradish peroxidase, (b) an acidic solution containing a protein denaturing agent. A preferred kit, according to the invention additionally comprises one or more microwell plates, a chromogenic, fluorogenic, or light emitting electron donor substrate, and an electron acceptor substrate. Also preferred, a kit contains peroxidase enzyme or an analyte binding agent (such as an antibody) conjugated to one or more peroxidase enzymes.

The following examples and figures are provided to aid the understanding of the present invention, the true scope of which is set forth in the appended claims. It is understood that modifications can be made in the procedures set forth without departing from the spirit of the invention.

SPECIFIC EMBODIMENTS

Example 1

Inhibition of High and Low Amounts of HRP Activity Using SDS, Sulfuric Acid, and Oxalic Acid Stop Reagents Jurkat cells were cultured and subsequently divided into two culture dishes. In one dish the cells were treated with 1 µg/ml CAM (Camptothecin) to induce apoptosis, thereby leading to the formation of mono and oligonucleosomes, the target antigen. After an incubation period of 4 hours the cells of both dishes were harvested separately by centrifugation, lysed by the detergent contained in the Cell Death Detection ELISA Plus (Roche Diagnostics GmbH, Mannheim, Germany; Catalogue No. 1920685), and frozen. The mono and oligonucleosomes consisting of DNA and histones H2A, H2B, H3 and H4 were detected in thawed cell homogenate by way of a sandwich ELISA. Antigen was captured with a first monoclonal antibody against histone from the Cell Death Detection ELISA Plus kit. The antibody was coated onto the walls of a 96-well microplate. The detection antibody was a DNA-specific polyclonal antibody conjugated with horseradish peroxidase.

Non-induced and CAM-induced Jurkat cells yielded low and high amounts of target antigen, thereby leading to low and high absolute amounts of horseradish peroxidase enzymatic activity in the respective wells.

Into each well of the 96-well microplate an aliquot of 100 µl of ABTS Solution (Roche Diagnostics GmbH, Mannheim, Germany; Roche Applied Science, product no. 11684302001) was added. After an incubation for 8 minutes at room temperature, 100 µl of either distilled water or a stop reagent as indicated in the legend to FIG. 1 was added. Absorbance was measured at 405 nm at the time points indicated in FIG. 1.

Figure 1B:
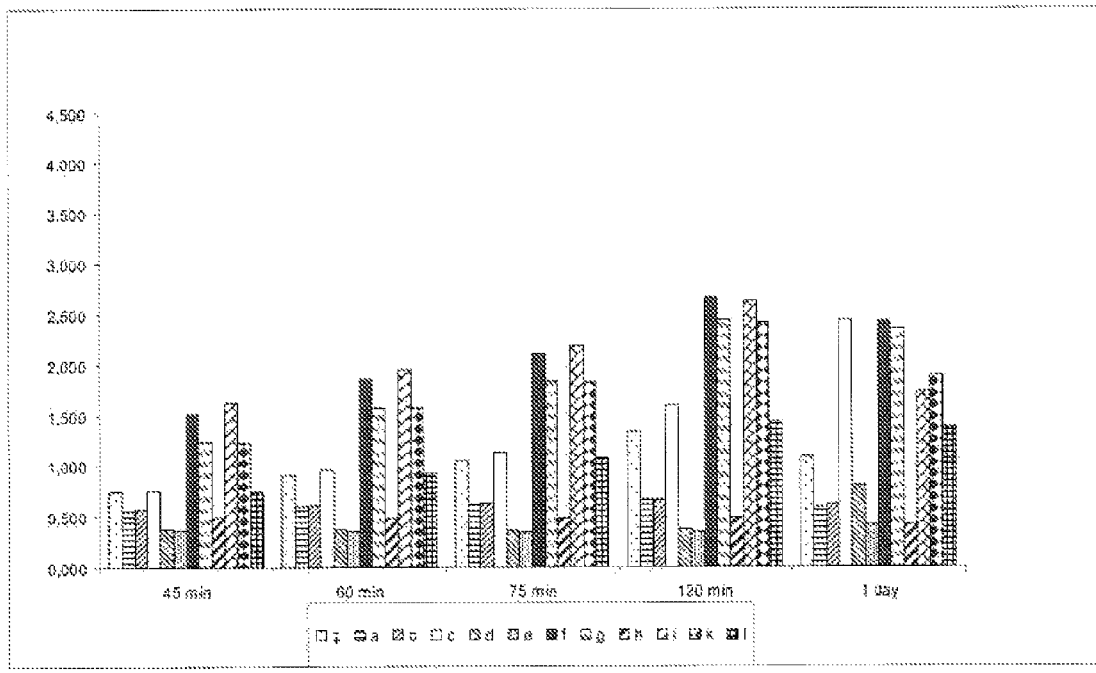
Figure 2A:
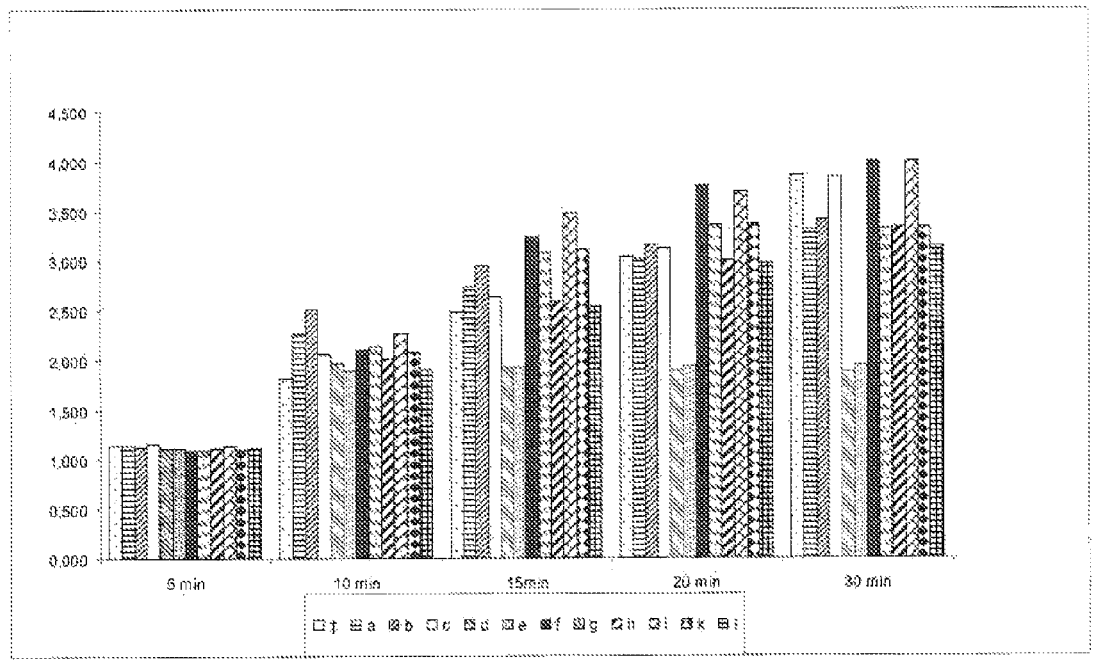
FIG. 2, A and B: inhibition of ABTS turnover catalyzed by a high amount of HRP detection of a high amount of mono- and oligosomes in Jurkat cells; further details are given in Example 1. All other designations are the same as in FIG. 1.
Figure 2B:
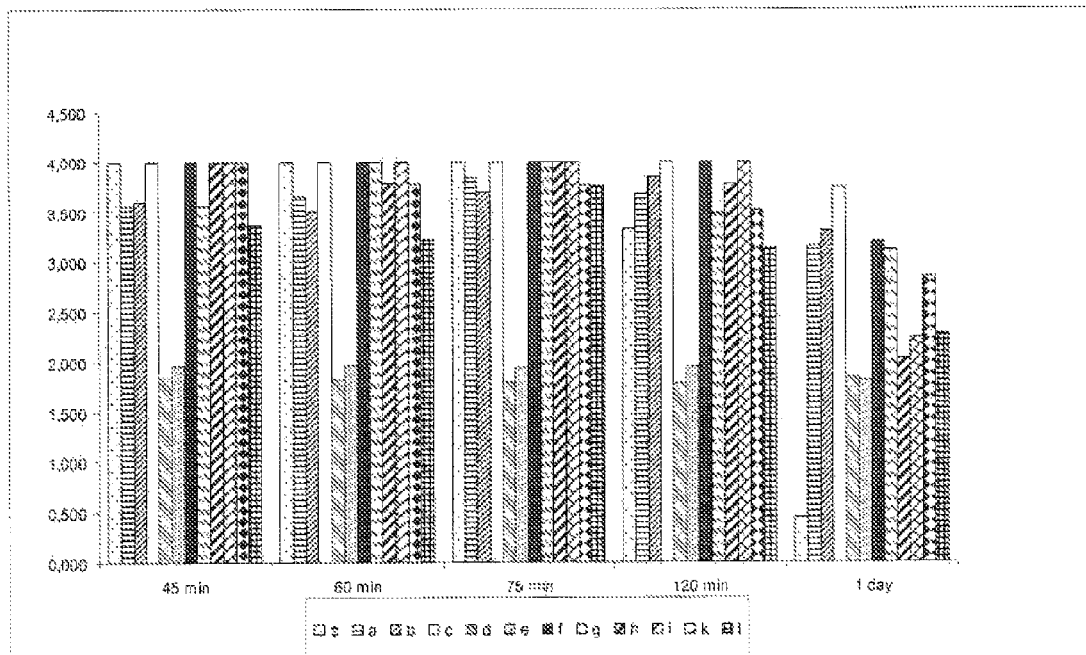

As can be seen in FIG. 1, SDS and high concentrations of oxalic acid or sulfuric acid lead to a complete inhibition of the reaction. In FIG. 2, however, it becomes clear that SDS and oxalic acid were not able to inhibit completely the high amount of HRP activity. In addition, $H_2SO_4$ and oxalic acid at high concentratios of 0.5 to 0.25M cause precipitation of the substrate.

Example 2

Inhibition of 1 mU of HRP Activity Using Heavy Metal Salts and Other Compounds as Stop Reagents Various described peroxidase inhibitor compounds as given in Table 1 were tested as stop reagents at the indicated concentrations with HRP in 100 µl of ABTS solution in a 96-well plate using a different experimental setting: HRP was added to the ABTS solution at an amount to yield an absolute peroxidase enzymatic activity of 1 mU per well. Stop reagent was added following an initial incubation of the ABTS/HRP mixture for 8 minutes at room temperature. For each stop reagent, several photometric readings were made after the time spans indicated in Table 2a and Table 2b. In these tables typical results of inhibition assays with the inhibitors of Table 1 are shown. When two different concentrations of an inhibitor were tested, only the result obtained with the higher concentration of the inhibitor was included in the tables. At the lower concentrations the inhibitors were not sufficiently effective when tested (data not shown).

TABLE 1

Inhibitors of HRP tested

| | Inhibitor: | 1st concentration | 2nd concentration |
|---|---|---|---|
| (i) | Manganese(II) carbonate | 0.25 mM | |
| (ii) | Lead(II) acetate | 0.5M | |
| (iii) | Cobalt(II) acetate | 0.5M | 0.05M |
| (iv) | Cadmium(II) sulfate | 0.5M | 0.05M |
| (v) | Iron(III) nitrate | 0.5M | |
| (vi) | Copper(II) sulfate | 0.5M | 0.05M |
| (vii) | Sodium orthovanadate | 0.5M | 0.05M |
| (viii) | NaF | 0.4M | |
| (ix) | Nickel(II) chloride | 0.1M | |
| (x) | Sodium azide | 0.25M | 0.025M |
| (xi) | Sodium Oxamate | 0.1M | |
| (xii) | KSCN | 0.1M | 0.05M |
| (xiii) | NaOH | 0.5M | 0.1M |

It was also noted that vanadate, sodium hydroxide, potassium thiocyanate and sodium azide resulted in a decoloration of the dye, whereas only NaF and the commercially available stop reagent (designated "comm." in Table 2b) effected inhibition, however only partially.

TABLE 2a

Absorbance at 405 nm after time intervals as indicated

| Time | ‡ | (i) | (ii) | (iii) | (iv) | (v) | (xiii) | (vi) |
|---|---|---|---|---|---|---|---|---|
| 6 min | 1.090 | 1.066 | 1.065 | 1.062 | 1.059 | 1.054 | 1.036 | 1.077 |
| 9 min | 1.413 | 1.560 | 1.864 | 1.471 | 1.759 | 3.999 | 0.878 | 1.646 |
| 15 min | 2.183 | 2.173 | 0.761 | 2.666 | 2.907 | 3.999 | 0.027 | 1.669 |
| 30 min | 3.255 | 3.260 | 1.900 | 2.666 | 3.999 | 3.999 | 0.027 | 1.767 |
| 45 min | 3.565 | 3.767 | 2.998 | 2.666 | 3.999 | 3.999 | 0.027 | 1.831 |
| 60 min | 3.763 | 3.999 | 3.999 | 2.666 | 3.999 | 3.999 | 0.027 | 1.765 |
| 180 min | 3.999 | 3.999 | 3.999 | n.d. [*] | 2.379 | 3.999 | 0.026 | 1.842 |

(‡) indicates the control: ABTS solution incubated without HRP, no stop reagent added.
[*] negative value deleted.

TABLE 2b

Absorbance at 405 nm after time intervals as indicated

| Time | ‡ | (vii) | (viii) | (ix) | (x) | (xi) | (xii) | comm. |
|---|---|---|---|---|---|---|---|---|
| 6 min | 1.189 | 1.173 | 1.176 | 1.175 | 1.172 | 1.182 | 1.179 | 1.159 |
| 9 min | 1.531 | 0.115 | 1.343 | 2.241 | 1.395 | 1.776 | 1.207 | 1.948 |
| 15 min | 2.459 | 0.096 | 1.424 | 2.999 | 0.111 | 2.525 | 1.290 | 2.453 |
| 30 min | 3.999 | 0.089 | 1.572 | 3.719 | 0.028 | 3.091 | 1.201 | 2.699 |
| 45 min | 3.999 | 0.088 | 1.721 | 3.999 | 0.026 | 3.097 | 1.086 | 2.704 |
| 60 min | 3.999 | 0.092 | 1.818 | 3.715 | 0.024 | 3.095 | 0.989 | 2.693 |
| 180 min | 3.999 | 0.100 | 2.107 | 3.999 | 0.024 | 2.865 | 0.849 | 2.634 |

(‡) indicates the control: ABTS solution incubated without HRP, no stop reagent added, "comm." indicates a commercially available stop reagent from KPL, Inc., Gaithersburg, MD. USA; catalogue no. 50-85-01

Example 3

Inhibition of 1 mU of HRP Activity Using Acidified SDS Solution as Stop Reagent A solution of 5% [w/v] sodium dodecyl sulfate acidified with 0.25 M hydrochloric acid was used as a stop reagent to inhibit 1 mU peroxidase enzymatic activity of HRP. The experimental setting was similar to that in Example 2, using an amount of 1 mU of HRP activity in 100 µl of ABTS solution, 100 µl of stop reagent were added.

TABLE 3

Absorbance at 405 nm after time intervals as indicated

| | ‡ (control) | 5% SDS/25 mM HCl |
|---|---|---|
| 5 min | 1.134 | 1.157 |
| 7 min | 1.378 | 1.866 |
| 10 min | 1.824 | 1.853 |
| 15 min | 2.902 | 1.841 |
| 30 min | 3.999 | 1.833 |
| 45 min | 3.999 | 1.833 |
| 60 min | 3.999 | 1.837 |
| 120 min | 3.999 | 1.845 |

(‡) indicates the control: ABTS solution incubated without HRP, no stop reagent added.

Another experiment was performed in which two different SDS concentrations 5% and 0.5% [w/v] in an acidified solution were compared.

TABLE 4

Absorbance at 405 nm after time intervals as indicated

| | ‡ (control) | 5% SDS/25 mM HCl | 0.5% SDS/25 mM HCl |
|---|---|---|---|
| 5 min | 0.848 | 0.850 | 0.846 |
| 7 min | 1.122 | 1.288 | 1.178 |

TABLE 4-continued

| | ‡ (control) | 5% SDS/25 mM HCl | 0.5% SDS/25 mM HCl |
|---|---|---|---|
| 10 min | 1.703 | 1.283 | 1.219 |
| 15 min | 2.507 | 1.284 | 1.246 |
| 30 min | 3.999 | 1.281 | 1.259 |
| 45 min | 3.745 | 1.273 | 1.250 |
| 60 min | 3.759 | 1.272 | 1.246 |

Absorbance at 405 nm after time intervals as indicated

It was found that acidification of the reaction mixture in the well to a ph value of about 2.5 to 4.2 in combination with SDS at a final concentration of between 0.25% and 2.5% weight by volume is very effective in inhibiting peroxidase enzymatic activity. At the same time, the concentration of the acidic component does not cause precipitation of the substrate.

What is claimed is:

1. A method for inhibiting peroxidase enzymatic activity in an aqueous solution comprising the steps of:
    providing an aqueous solution comprising a peroxidase enzyme, an electron acceptor substrate, and ABTS (2,2'-azino-di-(3-ethylbenzothiazoline-6-sulphonic acid) as an electron donor substrate, wherein the peroxidase enzyme catalyzes turnover of ABTS to yield a colored oxidized product of ABTS which can be measured spectrophotometrically, and
    adding an acidic stop reagent to the solution wherein the stop reagent comprises sodium dodecyl sulfate (SDS) and whereby the pH of the solution is adjusted to between about 2.5 and 4.2, and further whereby SDS is present in the solution at a concentration of between 0.25% and 2.5% weight by volume, thereby inhibiting the peroxidase enzymatic activity while stabilizing the oxidized product to avoid precipitation of the substrate and maintain the spectrophotometric measurement of the solution.

2. The method of claim 1 wherein the stop reagent further comprises a chaotropic substance selected from the group consisting of urea, guanidinium hydrochloride, guanidinium thiocyanate, and guanidinium isothiocyanate.

3. The method of claim 2 wherein the chaotropic substance has a concentration of 5% to 70% weight by volume.

4. The method according to claim 1, wherein the pH of the solution is adjusted with HCl.

5. The method according to claim 1, wherein the electron acceptor substrate comprises $H_2O_2$.

* * * * *